US00PP30044P3

(12) United States Plant Patent
Eveleens

(10) Patent No.: US PP30,044 P3
(45) Date of Patent: Jan. 1, 2019

(54) ***HYDRANGEA* PLANT NAMED 'HORTMAGITRI'**

(50) Latin Name: *Hydrangea macrophylla*
Varietal Denomination: Hortmagitri

(71) Applicants: Horteve Breeding BV, Aalsmeer (NL); Kolster Holding BV, Boskoop (NL)

(72) Inventor: Cornelis Pieter Eveleens, Aalsmeer (NL)

(73) Assignees: HORTEVE BREEDING B.V., Aalsmeer (NL), part interest; KOLSTER HOLDING B.V., Boskoop (NL), part interest ( * ) Notice: Subject to any disclaimer, the term of this patent is extended or adjusted under 35 U.S.C. 154(b) by 0 days.

(21) Appl. No.: 15/731,894

(22) Filed: Aug. 21, 2017

(65) Prior Publication Data

US 2018/0116084 P1 Apr. 26, 2018

(30) Foreign Application Priority Data

Oct. 21, 2016 (QZ) ..... PBR 2016/2547

(51) Int. Cl.
*A01H 5/00* (2018.01)
*A01H 5/02* (2018.01)

(52) U.S. Cl.
USPC ..... Plt./250
CPC ..... *A01H 5/02* (2013.01)

(58) Field of Classification Search
USPC ..... Plt./250
See application file for complete search history.

*Primary Examiner* — Susan McCormick Ewoldt
(74) *Attorney, Agent, or Firm* — Penny J. Aguirre

(57) ABSTRACT

A new cultivar of *Hydrangea macrophylla* plant named 'Hortmagitri' that is characterized by its mophead type inflorescences with sterile flower sepals that are red with a darker red flush in color, its sturdy and thick textured sterile flower sepals, and its good performance as a cut flower.

2 Drawing Sheets

Botanical classification: *Hydrangea macrophylla.*
Varietal denomination: 'Hortmagitri'.

CROSS REFERENCE TO A RELATED APPLICATION

This application is co-pending with a U.S. Plant Patent Application filed for a plant derived from the same breeding program that is entitled *Hydrangea* Plant Named 'Hortmalegretto' (U.S. Plant patent application Ser. No. co-pending 15/731,893).

BACKGROUND OF THE INVENTION

The present invention relates to a new and distinct cultivar of *Hydrangea macrophylla* and will be referred to hereafter by its cultivar name, 'Hortmagitri'. 'Hortmagitri' represents a new big leaf *hydrangea*, a perennial shrub grown for use as a landscape plant and for cut flower production.

'Hortmagitri' was derived from an ongoing controlled breeding program directed by the Inventor in Boskoop, The Netherlands. The objective of the breeding program was to develop new cultivars of *Hydrangea* with flowers that are dark red in color. 'Hortmagitri' arose from a controlled cross made by the Inventor in June of 2010 between unnamed and unpatented proprietary plants in the Inventor's breeding program; reference no. Erm-1 as the female parent and reference no. 08-036-19 as the male parent. 'Hortmagitri' was selected as a single unique plant from amongst the resulting seedlings in August of 2014.

Asexual propagation of the new cultivar was first accomplished by stem cuttings by the Inventor in Boskoop, The Netherlands in August of 2012. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hortmagitri' as a unique cultivar of *Hydrangea macrophylla.*

1. 'Hortmagitri' exhibits mophead type inflorescences with sterile flower sepals that are red with a darker red flush in color.
2. 'Hortmagitri' exhibits sturdy and thick textured sterile flower sepals.
3. 'Hortmagitri' performs well as a cut flower.

The female parent of 'Hortmagitri' differs from 'Hortmagitri' in having sterile flower sepals that are less sturdy and thick textured and leaves that are larger in size. The male parent of 'Hortmagitri' differs from 'Hortmagitri' in having flowers that are pink and green in color, leaves that are larger in size and a more flattened inflorescence. 'Hortmagitri' can be most closely compared to the *Hydrangea macrophylla* cultivars 'Kolmaru' (U.S. Plant Pat. No. 25,104) and 'Hortmalegretto'. 'Kolmaru' is similar to 'Hortmagitri' in having inflorescences with sterile sepals that is red in color. 'Kolmaru' differs from 'Hortmagitri' in having sterile flower sepals that lack a darker red flush and that are less sturdy and thick textured and in having leaves that are larger in size. 'Hortmalegretto' is similar to 'Hortmagitri' in having inflorescences with sterile sepals that are red in color and thick textured. 'Hortmalegretto' differs from 'Hortmagitri' in having sterile sepals that are brighter red in color and that lack darker red markings.

BRIEF DESCRIPTION OF THE DRAWINGS

The accompanying colored photographs illustrate the overall appearance and distinct characteristics of the new *Hydrangea*. The photographs were taken of a plant two years in age as grown in a 17-cm container in a greenhouse in Boskoop, The Netherlands.

The photograph in FIG. 1 provides a side view of the plant habit of 'Hortmagitri' in bloom.

Figure 1:
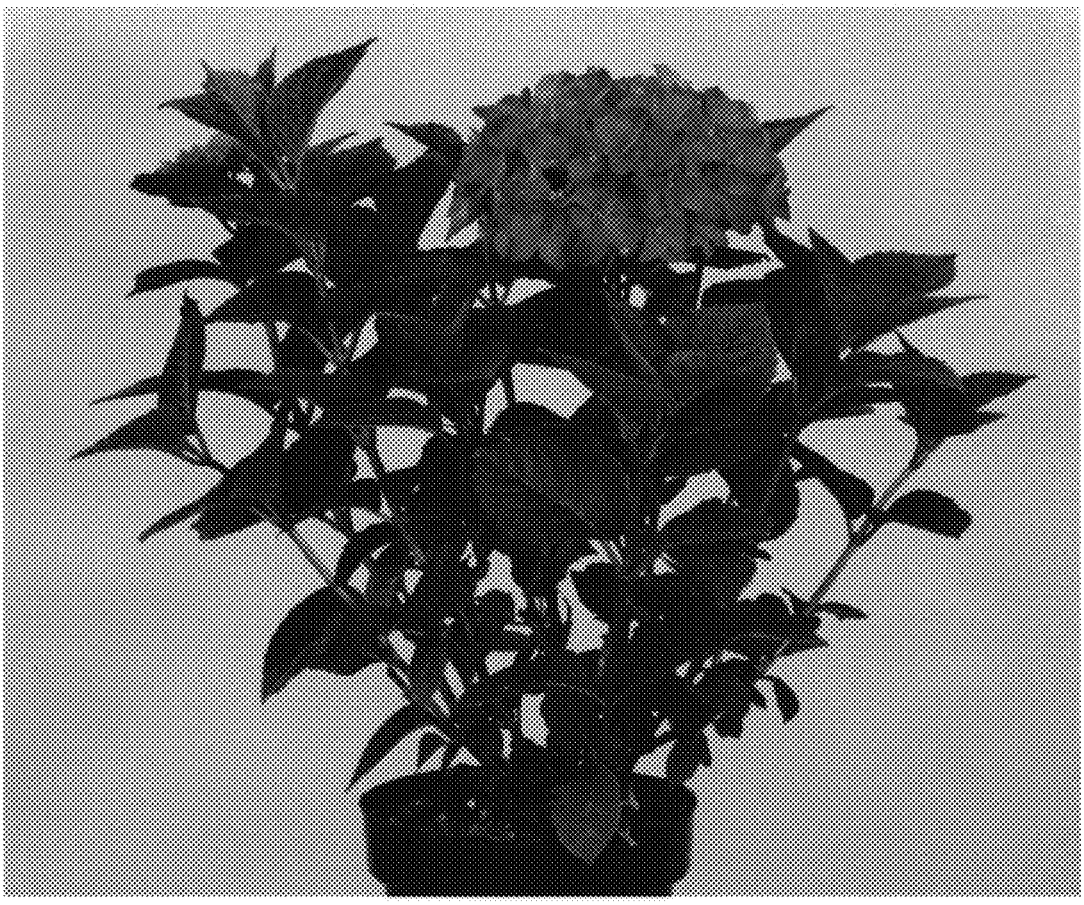
Figure 2:
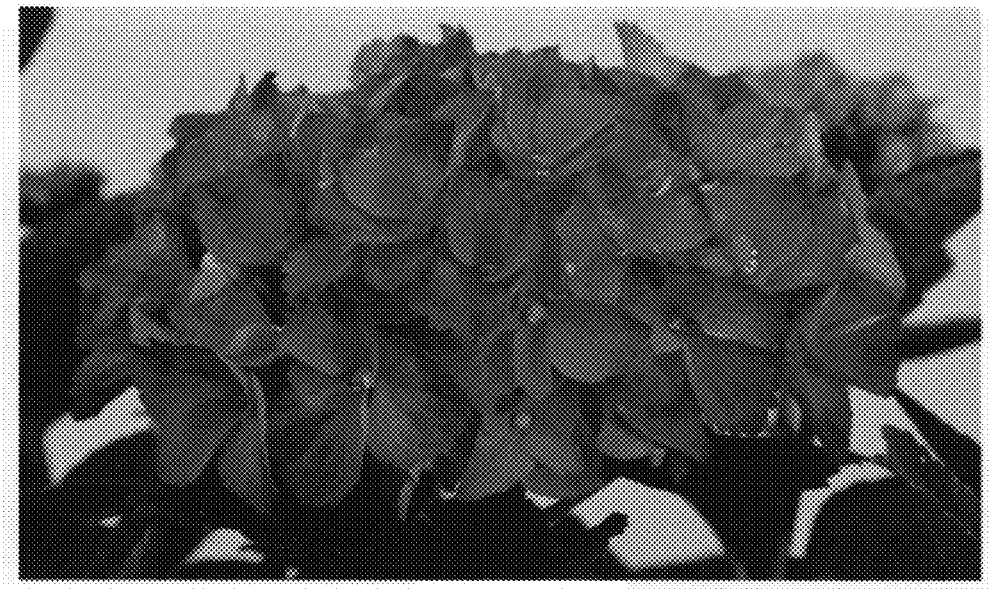

The photograph in FIG. 2 provides a close-up view of an inflorescence of 'Hortmagitri'.

Figure 3:
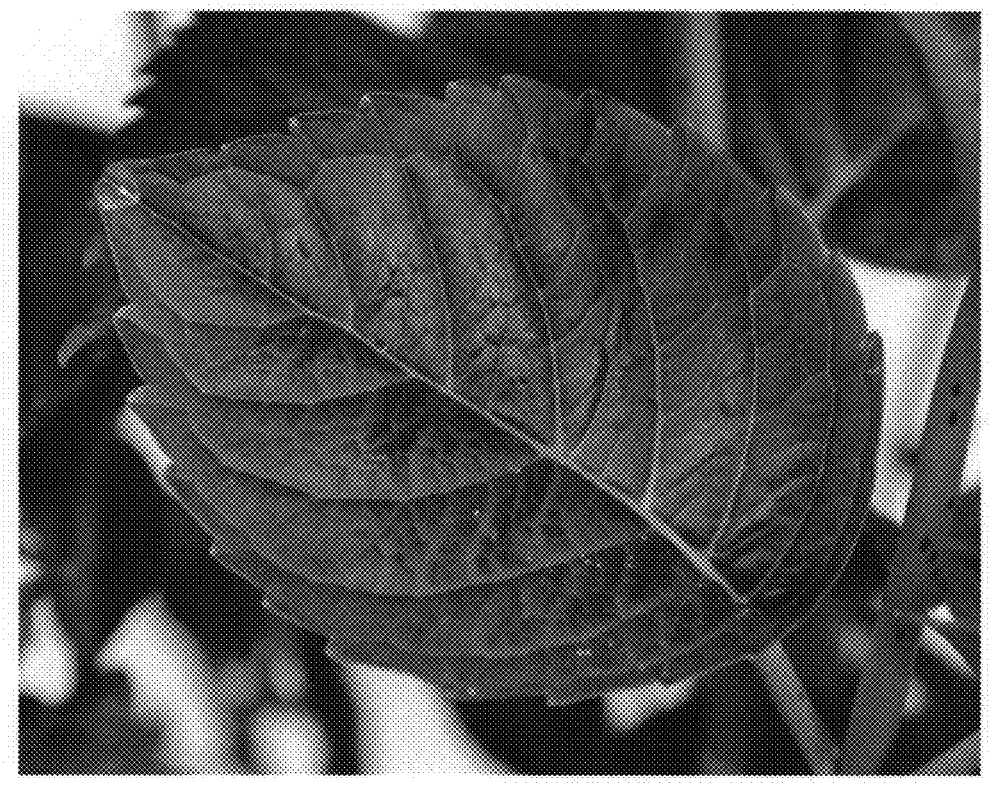

The photograph in FIG. 3 provides a close-up view of a leaf of 'Hortmagitri'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants two years in age as grown in 17-cm containers in a greenhouse in in May in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—From spring to late summer in The Netherlands.

*Plant type.*—Perennial shrub, mophead type *hydrangea.*

*Plant habit.*—Broadly spreading to upright.

*Height and spread.*—An average of 45.5 cm in height and 54.8 cm in spread as grown in a 17-cm container about 1 m in height and width as a 3 year-old plant in the landscape.

*Hardiness.*—At least in U.S.D.A. Zones 5 to 9.

*Diseases and pests.*—No susceptibility or resistance to pests and diseases has been observed.

*Root description.*—Fibrous and fine, 199D in color.

*Propagation.*—Stem cuttings.

*Time required for root development.*—An average of 3.5 weeks for root initiation with a young rooted plant produced in an average of six months.

*Growth rate.*—Moderate.

Stem description:

*Stem shape.*—Rounded.

*Stem strength.*—Strong.

*Stem aspect.*—Upright to an average angle of 70° to soil.

*Stem color.*—Immature stems; 143B, mature stems; between 143B and 144A, internodes between N186B and N186C, older bark; 199A to 199B.

*Stem size.*—An average of 27.8 cm (excluding the inflorescence) in length and 6 mm in diameter.

*Stem surface.*—Immature and mature stems; glabrous and densely lenticellate with lenticels; an average of 2 mm in length, 1 mm in width, color between N186B and N186C.

*Branching.*—Freely branched with an average of 14 lateral branches, branching improves with pinching.

*Internode length.*—An average of 6.7 cm.

Foliage description:

*Leaf shape.*—Broadly ovate.

*Leaf arrangement.*—Opposite.

*Leaf division.*—Simple.

*Leaf number.*—An average of 14 (7 pairs) per lateral branch.

*Leaf base.*—Truncate.

*Leaf apex.*—Apiculate.

*Leaf margins.*—Serrate to dentate.

*Leaf venation.*—Pinnate, color; upper surface 144A, lower surface 144B, lower surface main veins are covered with short hairs; an average of 0.2 mm in length, too small to measure color.

*Leaf size.*—An average of 10.5 cm in length and 7.9 cm in width.

*Leaf attachment.*—Petiolate.

*Leaf surface.*—Upper and lower surfaces; smooth and moderately rugose.

*Leaf color.*—Young leaves; upper and lower surface 143A, mature upper surface between NN137A and 147A, mature lower surface between 138A and 147B.

*Petioles.*—An average of 1.6 cm in length and 3.5 mm in diameter, color; upper surface 144B, lower surface 143C, both surfaces; smooth and slightly glossy, strong.

Inflorescence description:

*Inflorescence type.*—Mophead type, flattened globular in shape, compound corymb of rotate-shaped sterile flowers over fertile flowers.

*Lastingness of inflorescence.*—Sterile flowers; an average of 6 weeks, persistent, fertile flowers; an average of 1 week, self-cleaning.

*Lastingness as a cut flower.*—About 2 weeks in full color, longer as a drying inflorescence.

*Inflorescence number.*—One per lateral stem.

*Inflorescence size.*—An average of 10.3 cm in height and 16.9 cm in diameter.

*Flower number.*—An average of 100 sterile flowers and 40 fertile flowers per inflorescence.

*Flower fragrance.*—None.

*Flower aspect.*—Sterile flowers; upright, outwards, and slightly drooping, fertile flowers; upright.

*Flower size.*—Sterile flowers; an average of 4.7 cm in diameter and 2 cm in depth, fertile flowers; an average of 8 mm in diameter and 4 mm in depth.

*Flower shape.*—Sterile flowers; rotate and slightly cup-shaped, fertile flowers; rotate, petals dropped when maturing.

*Flower buds.*—Sterile flowers; an average of 3 mm in length and diameter, globular in shape, color; 64D, fertile flowers; an average of 5.5 mm in length and 4 mm in diameter, obovate in shape, color; 64D with base 145B.

*Peduncles.*—An average of 9 cm in length and 8 mm in diameter, held upright to outwards, 181D, smooth surface, strong.

*Pedicels.*—Sterile flowers; an average of 2.2 cm in length and 2 mm in diameter, held at an average angle of 40° to peduncle, 60D in color, moderate strength, dull surface is moderately covered with thin hairs; an average of 0.2 mm in length and too small to measure color, fertile flowers; an average of 3 mm in length and 1 mm in diameter, held at an average angle of 15° to vertical, 181D in color, moderate strength, dull surface moderately covered with thin pubescence 0.2 mm in length and too small to measure color.

*Petals.*—Sterile flowers; average of 4, rotate, ovate in shape, concave, acute apex, cuneate base, entire margin, an average of 4 mm in length and 2.5 mm in width, glabrous and dull upper and lower surfaces, color when opening and when fully open upper and lower surface; 64D, fertile flowers; average of 5, occasionally 4, rotate, ovate in shape, concave, acute apex, cuneate base, entire margin, an average of 4 mm in length and 2.5 mm in width, glabrous and dull upper and lower surfaces, color when opening and when fully open upper and lower surface; 64D.

*Sepals.*—Sterile flowers; an average of 4, occasionally 3, rotate (cross-like) in arrangement, near deltoid to broad ovate in shape, apex is bluntly acute to obtuse, truncate base, margin entire to slightly irregularly dentate to serrate, an average of 2.6 cm in length and 3 cm in width, color; upper surface when opening 61C, upper surface when opening 64D, upper surface when fully open between 59C and 60A, fading to 59C and strongly tinged 200A to 200B at the tip, lower surface when fully open between 59D and 63B, fading to 63B to 63C and strongly tinged 148A at the tips, both surfaces glabrous and dull, fertile flowers; an average of 5, rotate in arrangement, broad ovate in shape, acute apex, broadly cuneate base, entire margin, an average of 3 mm in length and 2 mm in width, color; upper surface when opening and when fully open 144C, flushed with 63D, lower surface when opening and when fully open 144B, flushed with 63C, both surfaces glabrous and dull.

Reproductive organs:

*Gynoecium.*—Sterile flowers; 2 pistils, an average of 1 mm in length, stigma; club-shaped and 155D in color, style; 0.5 mm in length, 63D in color, ovary is 150D in color, fertile flowers; an average of 3 pistils; an average of 1 mm in length, stigma; club-shaped and 155D in color, style; 0.5 mm in length, 63D in color, ovary is between 150C and 150D in color.

*Androecium.*—Sterile flowers; an average of 8 stamens, filaments; an average of 3 mm in length and N155B in color, anthers; oblong in shape, an average of 1 mm in length and 155B in color, pollen; moderate in quantity, 159D in color, fertile flowers; an average of 10 stamens, filaments; an average of 4 mm in length and 73D in color, anthers; oblong in shape, an average of 1 mm in length and 155A in color, pollen; moderate in quantity, 159D in color.

*Fruit and seed.*—No seeds or fruit observed to date.

It is claimed:

1. A new and distinct cultivar of *Hydrangea* plant named 'Hortmagitri' substantially as herein illustrated and described.

* * * * *